United States Patent [19]

Christou et al.

[11] Patent Number: 5,015,580

[45] Date of Patent: May 14, 1991

[54] PARTICLE-MEDIATED TRANSFORMATION OF SOYBEAN PLANTS AND LINES

[75] Inventors: Paul Christou, Madison; Dennis McCabe, Middleton; William F. Swain, Madison; Kenneth A. Barton, Middleton, all of Wis.

[73] Assignee: Agracetus, Middleton, Wis.

[21] Appl. No.: 193,357

[22] Filed: May 12, 1988

Related U.S. Application Data

[63] Continuation-in-part of Ser. No. 79,658, Jul. 29, 1987, abandoned.

[51] Int. Cl.$^5$ .................. C12N 15/00; C12N 5/00; A01H 1/00
[52] U.S. Cl. .................. 435/172.3; 435/172.1; 435/240.45; 435/240.47; 435/240.48; 435/240.5; 435/317.1; 435/320.1; 935/30; 935/52; 935/53; 935/67; 935/85; 800/205; 800/DIG. 26
[58] Field of Search .............. 435/172.3, 240.5, 172.1; 935/52, 53, 85; 800/205

[56] References Cited

U.S. PATENT DOCUMENTS 4,857,465 8/1989 Barwale et al. ................. 435/240.5
4,945,050 7/1990 Sanford et al. .................. 435/240.4

FOREIGN PATENT DOCUMENTS 2560744 9/1985 European Pat. Off. .
0256751 2/1988 European Pat. Off. .
0270356 6/1988 European Pat. Off. .

OTHER PUBLICATIONS

Klein et al. (1985) Program and Abstracts for Symposium on Biotechnology in Plant Science, Cornell Unw., Ithaca, NY, Poster #28.
Klein et al. (1987) Nature 327: 70–73.
Fraley et al. (1983) Proc. Nat. Acad. Sci, USA 80:4803–4807.
Potrykus 1990. Bio/Tech. 8:535–542.
Ow et al. 1986, Science 234: 856–859.
Cheng, et al., Plant Regeneration From Soybean Cotyledonary Node Segments in Culture, *Plant Science Letters*, 19: 91–99 (1980).
Christou, et al., Soybean Genetic Engineering–Commercial Production of Transgenic Plants, *Trends in Biotechnology*, Jun. 1990 vol. 8, No. 6.
Christou et al., Inheritance and Expression of Foreign Genes in Transgenic Soybean Plants, *Proc. Natl. Acad. Sci. USA*, vol. 86, pp. 7500–7504, (Oct. 1989).
Lippmann et al., Induction of Somatic Embryos in Cotyledonary Tissue of Soybean, Glycine Max L. Merr., *Plant Cell Reports* (1984 3:215–218).
McCabe et al., Stable Transformation of Soybean *Glycine Max*) by Particle Acceleration, *Bio/Technology*, vol. 6, Aug. 1988.
Phillips et al., Induction and Development of Somatic Embryos from Cell Suspension Cultures of Soybean, *Plant Cell Tissue Organ Culture* 1:123–239 (1981).
Saka, et al., Stimulation of Multiple Shoot Formation on Soybean Stem Nodes in Culture, *Plant Science Letters*, 19:193–201 (1980).

(List continued on next page.)

*Primary Examiner*—Elizabeth C. Weimar
*Assistant Examiner*—Rhodes P.
*Attorney, Agent, or Firm*—Quarles & Brady

[57] ABSTRACT

A method and apparatus is disclosed for the genetic transformation of soybean plants and plant lines by particle mediated transformation. Foreign genes are introduced into regenerable soybean tissues by coating on carrier particles which are physically accelerated into plant tissues. The treated plant tissues are then recovered and regenerated into whole sexually mature plants. The progeny are recovered from seed set by these plants and a portion of these progeny will contain in their genome the foreign gene. The procedure may be used to create novel genetically engineered soybean plants and lines.

24 Claims, 7 Drawing Sheets

OTHER PUBLICATIONS

Sanford et al., Delivery of Substances into Cells and Tissues Using a Particle Bombardment Process, *Particle Science and Technology* 5:27-37 (1987).

Christou et al., Stable Transformation of Soybean Callus by DNA-Coated Gold Particles, *Plant Physiol.* 87, 671-674 (1988).

Wang et al., Transforamtion of Rice, Wheat and Soybean by the Microprojectile Method, *Journal of Cellular Biochemistry*, UCLA Symposia on Molecular & Cellular Biology, Supplement 12C, 1988.

"The Complete Nucleotide Sequence of an Infectious Clone of Cauliflower Mosaic Virus by M13m 7 Shotgun Sequencing", Gardner, et al., *Nucleic Acids Research* 9:12,2871-2888(1981).

"Supercoiled Circular DNA-Protein Complex in *Escherichia Coil*: Purification and Induced Conversion to an Open Circular DNA Form", Clewell and Helinski, *Proc. Nat. Acad. Sci. USA* 62:1159-1166 (1969).

"Factors Influencing Gene Delivery into Zea Mays Cells by High-Velocity Microprojectiles", Klein, et al., *Bio/Technology* 6:559-570 (1988).

"Biotechnology in Plant Science: Relevance to Agriculture in the Eighties", Held Jun. 23-27, 1985 in Ithaca, New York.

"Particle Gun Technology: A Novel Method for the Introduction of DAN into Living Cells", Klein, et al.

"Stable Transformation of Soybean (*Glycine Max*) by particle Acceleration", by the Inventors Here.

"Genetically Transformed Cotton (Gossypium Hirsutum L.) Plants", Umbeck, et al., *Bio/Technology* 5:263-266 (1987).

"Efficient Transfer of a Glyphosate Tolerance Gene Into Tomato Using a Binary *Agrobacterium Tumefaciens* Vector", Fillatti, et al., *Bio/Technology* 5:726-730 (1987).

"Leaf Disc transformation of Cultivated Tomato (*L. Esculentum*) Using *Agrobacterium tumefaciens*", McCormick, et al., *Plant Cell Reports* 5:81-84 (1986).

"Stable Transformation of Soybean by Elecroporation and Root Formation From Transformed Callus", Christou, et al., *Proc. Natl. Acad. Sci. USA* 84:3962-3966 (1987).

"Stable Transformation of Soybean Callus by DNA Coated Gold Particles", Christou et al., *Plant Physiology* (in press).

"High-Velocity Microprojectiles for Deliverying Nucleic Acids Into Living Cells", Klein, et al., *Nature* 327:70-73 (1987).

"Plant Regeneration From Callus Cultures of Several Soybean Genotypes via Embryogenesis and Organogenesis", Barwale, et al., *Planta* 167:473-481 (1986).

"Gus Fusions: B-Glucuronidase as a Sensitive and Versatile Gene Fusion Maker in Higher Plants", Jefferson, et al., *The Embo J.* 6:3901-3907 (1987).

"Nucleotide Sequence and Exact Localization of the Neomycin Phosphotransferase Gene From Transposon Tn6", Beck, et al., Gene 19:324-336 (1982).

"Plant Regeneration From Embryo-Derived Tissue Cultures of Soybeans", Ranch, et al., *In Vitro Cellular & Developmental Biology* 21:653-698 (1985).

"Stimulation of Multiple Shoot Formation on Soybean Stem Nodes in Culture", Saka et al., *Plant Science Letters* 19: 193-201 (1980).

"Genotypic Variability of Soybean Response to Agrobacterium Strains Harboring the Ti or RI Plasmids", Owens et al., *Plant Physiol.* 77:87-94 (1985).

"Induction and in Vitro Culture of Soybean Crown Gall Tumors", Pedersen et al., *Plant Cell Reports* 2:201-204 (1983).

"Establishment of T-DNA-Containing Soybean Cell Liens", Xiangcun et al., *Scientia Sinica* 29:374-377 (1986).

"Light-Inducible Expression of a Chimeric Gene in Soybean Tissue Transformed With Agrobacterium", Facciotti et al., *Bio/Technology* 3:241-246 (1985).

"Transformation of Cultivated Alfalfa Using Disarmed *Agrobacterium Tumefaciens*", Shahin et al., *Crop Science 26:1236-1239 (1986)*.

"Transgenic Rye Plants Obtained by Injecting DNA Into Young Floral Tillers", de la Pena et al., *Nature* 325:274-276 (1987).

"Expression of a Foreign Gene in Callus Derived From DNA-Treated Protoplasts of Rice (*Oryza sativa L.*)", Uchimiya et al., *Mol. Gen Genet.* 204:204-207 (1986).

"Plant Regeneration From Protoplast-Derived Callus of Rice (*Oryza sativa L.*)", Yamada et al., *Plant Cell Reports* 5:85-88 (1986).

"Efficient Plant Regeneration From Rice Protoplasts Through Somatic Embryogenesis", Abdullah et al., *Bio/Technology* 4:1087-1990 (1986).

"A Procedure for Plant Regeneration From Immature Cotyledon Tissue of Soybean", Lazzri et al., *Plant Mol. Biol. Reporter* 3:160-167 (1985).

(List continued on next page.)

OTHER PUBLICATIONS

"*Bacillus thuringiensis* D-Endotoxin Expressed in Transgenic *Nicotiana tabacum* Provides Resistance to Lepidopteran insects", Barton et al., *Plant Physiology* 85:1103-1109 (1987).

"B-Gluchuronidase From *Escherichia coli* as a Gene-Fusion Marker", Jefferson et al., *Proc. Natl. Acad. Sci. USA* 83:8447-8451 (1986).

"Dot Assay for Neomycin Phosphotransferase Activity in Crude Cell Extracts", Platt et al., *Anal. Biochem.* 162:529-533 (1987).

"A New Sensitive Method for Qualitative and Quantitative Assay of Neomycin Phosphotransferase in Crude Cell Extracts", Reiss et al., *Gene.* 30:211-218 (1984).

"Assaying Chimeric Genes in Plant, The GUS Gene Fusion Systems", Jefferson, et al., *Plant Molecular Biol. Reporter* 5:387-405 (1987).

"Isolation of Plant DNA and RNA", Taylor and Powell, *Focus* 4:4-6 (1982).

"Detection of Specific Sequences Among DNA Fragments Separated by Gel Electrophoresis", Southern, *J. Mol. Biol.* 98:503-517 (1975).

"Genomic Sequencing", Church and Gilbert, *Proc. Natl. Acad. Sci. USA 81:1991-1995 (1984).*

"Nuclear DNA Amounts in Angiosperms", Bennett et al., *Philos. Trans. R. Soc. London Ser. B.* 274:227-274 (1976).

PARTICLE-MEDIATED TRANSFORMATION OF SOYBEAN PLANTS AND LINES

CROSS-REFERENCE TO RELATED APPLICATION

This application is a continuation-in-part of Ser. No. 079,658 filed July 29, 1987.

FIELD OF THE INVENTION

The present invention relates to the general field of genetic engineering of plants and relates, in particular to the transformation of exogenous genetic material into the germ line of soybean plant lines by physically introducing the genetic material into regenerable tissues of soybean plant by particle-mediated transformation.

BACKGROUND OF THE INVENTION

There exists much current effort and research being expended toward the genetic transformation of plant species. It is believed that the development of efficient means for transforming foreign genes into plant germ lines will allow the diversity of the genetic stock in commercially important crop species to be widened and to allow functional genes of specific interest to be selectively introduced into crop species. The effort and research to date on the transformation, or genetic engineering, of plant species has achieved results which vary quite dramatically depending on the species of plant.

The principal mechanism which has been used heretofore for the introduction of exogenous genes into plants has begun with the transformation of single plant cells, either as protoplasts, or in an undifferentiated tissue mass known as a callus. Chimeric genes functional in plant cells have been introduced into single cell plant protoplasts by electroporation and microinjection. However, the most widely used transformation technique to date has taken advantage of a natural trait of the plant pathogen *Agrobacterium tumefaciens*, which has the innate ability to transfer a portion of the DNA from a Ti (Tumor-inducing) plasmid harbored in it into an infected plant cell. By inserting foreign genes into plasmids in Agrobacterium which carry certain sequences from the Ti plasmid, the bacterial transformational trait can be used to transport the foreign genes into the genome of the infected plant cells. Agrobacterium-mediated plant cell transformation has been found to work reasonably well in many model crop species, such as tobacco, petunia and carrot, but does suffer from several significant limitations. The first limitation is that the transformation can only be done on a tissue culture level, typically with somatic tissues, which then must be regenerated artificially into a whole plant. This limits the applicability of Agrobacterium-mediated genetic transformation to those crop species which can readily be regenerated from types of tissues which are susceptible to Agrobacterium infection. This limitation can also make Agrobacterium-mediated transformation a laborious process since the regeneration of some plants, even though possible, can be a long labor-intensive process requiring much skill and often some art. A second limitation is that the natural host range of Agrobacterium includes only dicotyledonous plants and a limited number of monocot species of the Liliaceae family. Therefore Agrobacterium-mediated transformation has not been proven to be an effective tool for monocot species of commercial interest, such as the cereal crop species.

Another difficulty with Agrobacterium-mediated transformations is the generation of somoclonal variants, which spontaneously arise in plant tissues in tissue culture, which may complicate identification of transformants.

It has been demonstrated that at least some chimeric gene constructions are effective for expression of foreign genes in many popular crop plant cells. The functionality of these chimeric constructions in monocots as well as dicots has been demonstrated by the transformation of maize as well as soybean protoplasts in culture through such techniques as electroporation. Christou et al., *Proc. Natl. Acad. Sci., USA*, 84:3962-3966 (1987). However, no currently known methodology exists to regenerate whole soybean plants, or whole fertile plants of several other important crop species, from such protoplasts. No whole, intact transformed soybean plants, for example, are known to have been regenerated from protoplast. Nevertheless genetic transformation of lines of soybean and other crop species is a desired objective because of the great agricultural value of the common crop plants and the potential to improve their value and productivity.

In essence, most strategies directed toward the genetic engineering of plant lines involve what generally may be considered two complementary processes. The first process involves the genetic transformation of one or more plant cells of a specifically characterized type. The transformation process is normally defined as introducing a foreign gene, usually a chimeric one, into the genome of the individual plant cells, as typically occurs during Agrobacterium-mediated transformation. The second process involves the regeneration or cultivation of the transformed plant cells into whole sexually competent plants. Neither aspect of the overall strategy is required to be 100 percent successful, or near thereto, but each aspect must have a reasonable degree of reliability and reproducibility so that a practical number of transformed plants can be recovered.

The two processes, transformation and regeneration, must be complementary. It is clearly possible to transform certain tissue or cell types from which the technology does not presently exist to regenerate them into whole plants. For example, it is readily possible, using the technique of electroporation, to readily transform soybean protoplast cells in vitro with foreign genes. However, soybean protoplasts cannot be regenerated. It is also possible to regenerate plant tissues of a number of different tissue and cell type for which no technique has presently been developed for successfully, genetically transforming them. The complementarity of the two halves of this overall procedure must then be such that the tissues which are successfully genetically transformed by the transformation process must be of a type and character and must be in sufficient health, competency and vitality, so that they can be successfully regenerated into a fertile whole plant or successfully used to create germ line plasma so that a whole intact fertile plant containing the foreign gene can be created.

Efforts have been previously made specifically directed to the genetic transformation of soybean cells in culture using *Agrobacterium tumefaciens*. For example, in Owens et al., *Plant Physiology.*, 77, 87-94 (1985) the responsiveness of soybean cells to *A. tumefaciens* infections was reported and in Facciotti et al., *Bio/Technology*, 3, 241-246 (1985) the expression of a chimeric gene in soybean crown gall cultures transformed with

*A. tumefaciens* was reported. Other similar reports suggested that tissues of soybeans can be transformed with oncogenic *A. tumefaciens*, although it has generally been acknowledged that such tissues are considered to be non-regenerable.

Significant effort has been directed toward the regeneration of soybean plants from various tissue types. Regeneration techniques for plants such as soybeans use as the starting material a variety of tissue or cell types. With soybeans in particular, regeneration processes have been developed that begin with certain differentiated tissue types such as meristems, Cartha et al., *Can. J. Bot.*, 59, 1671-1679 (1981), hypocotyl sections, Cameya et al., *Plant Science Letters*, 21, 289-294 (1981), and stem node segments, Saka et al., *Plant Science Letters*, 19, 193-201, (1980) and Cheng et al., *Plant Science Letters*, 19, 91-99 (1980). There has also been reported the regeneration of whole sexually mature soybean plants from somatic embryos generated from explants of immature soybean embryos Ranch et al., *In Vitro Cellular & Developmental Biology*, 21: 11, 653-658 (1985). Recent reports also describe the regeneration of mature soybean plants from tissue culture by organogenesis and embryogenesis, Barwale et al., *Planta*, 167, 473-481 (1986) and Wright et al., *Plant Cell Reports*, 5, 150-154 (1986).

There has been one report on the use of DNA-coated tungsten projectiles accelerated by a bullet gun to obtain transient expression of foreign DNA in intact epidermal cells of *Allium cepa* (onion), but no engineered plants have been reported from this method; Klein et al., *Nature*, 327:70-73 (1987).

SUMMARY OF THE INVENTION

The present invention is summarized in that a method of making a genetically transformed soybean plant includes the steps of: preparing copies of a foreign gene including a coding region and flanking regulatory sequences effective to express the coding region in soybean cells; joining copies of the foreign gene to biologically inert carrier particles; placing a regenerable soybean tissue on a target surface; physically accelerating the particles carrying the foreign gene copies at the target surface in such a fashion that some particles lodge in the interior of at least some of the cells of the soybean tissues; regenerating the treated tissue into a whole sexually mature soybean plant; and verifying the existence of the foreign gene in the tissues of the regenerated plant.

The present invention is also summarized in that soybean plants, and their seeds, are created carrying in their genome a foreign gene capable of expression in the cells of the soybean plant.

It is thus an object of the present invention to provide an efficient and replicable process for genetically engineering soybean plants and lines.

It is a feature of the present invention that a wide variety of soybean tissue types may be used in the process to successfully create transformed soybean plants.

Other objects, advantages and features will become apparent from the following specification.

DETAILED DESCRIPTION OF THE INVENTION

In the practice of plant genetic transformation conducted in accordance with the present invention, DNA is physically delivered into the interior of meristematic or embryonic soybean cells, the DNA being carried into individual cells, but neither destroying nor incapacitating them. It has been found that DNA delivered in such a fashion into soybean cells can be stably integrated into the genetic heritage of the resulting plants and plant lines.

There are several factors which influence successful soybean cell transformations conducted in this fashion. The tissues into which the genes are inserted must be capable of being regenerated into whole sexually mature plants. The manner in which the DNA is carried into the cells is by loading onto particles which are accelerated in a carefully arranged fashion so that the individual DNA-bearing particles have a proper momentum and velocity, and are in a relatively uniform pattern, so that when contacting the plant tissue, the particles penetrate into the interior of a significant number of living cells without biologically disabling them. Furthermore, the DNA on the particles should be capable of transforming soybean cells and expressing the desirable trait in the plant cells. In addition, the DNA itself may contain a selectable or screenable marker which can be detected in putatively transformed plant tissues, seeds or plantlets in order to verify the specific plant tissues in which genetic transformation has occurred. If the transformation frequency is high enough, such a selectable marker may not be necessary, since the presence of the introduced DNA can usually be detected by biochemical analysis.

Figure 1:
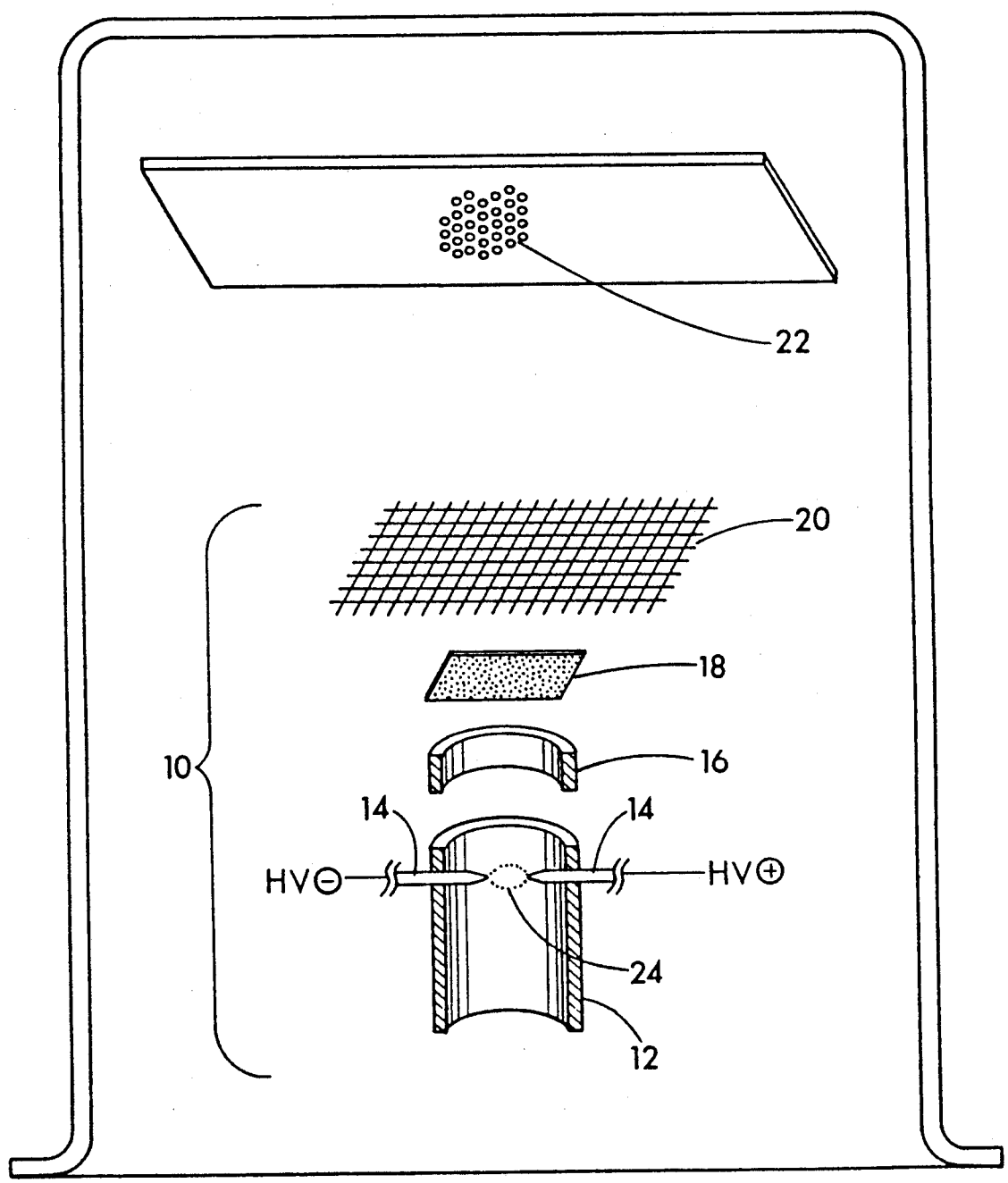
FIG. 1 is an exploded sectional view of one embodiment of a particle accelerator suitable for use in the present invention.
Figure 2:
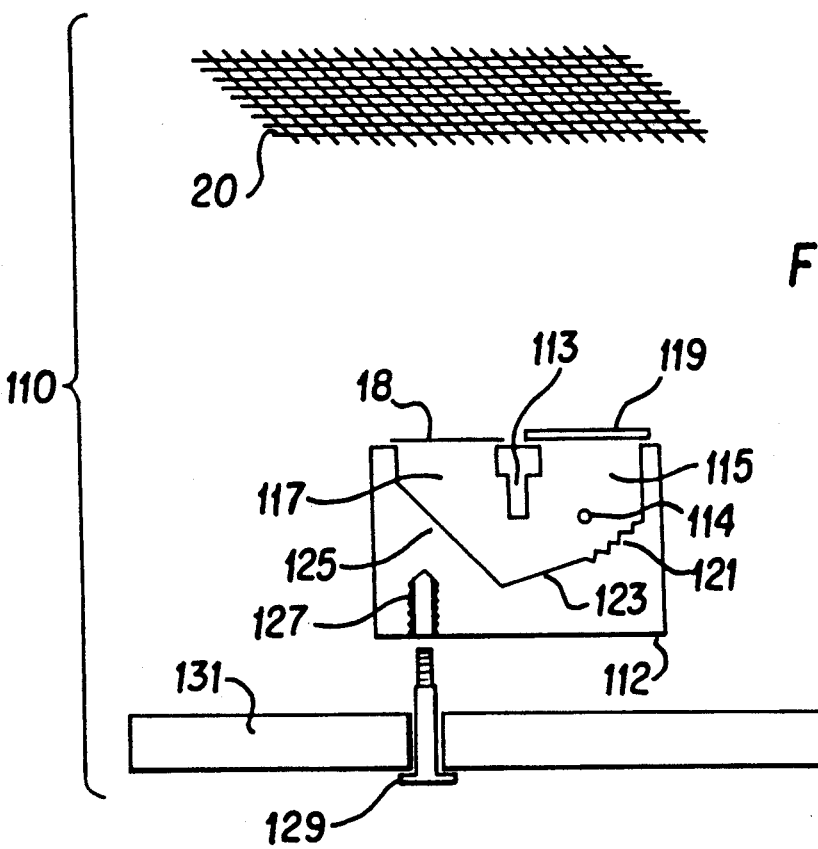
FIG. 2 is an exploded sectional view of another embodiment of a particle accelerator suitable for use in the present invention.
Figure 3:
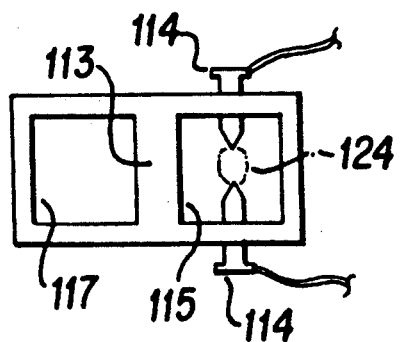
FIG. 3 is a top plan view of the discharge chamber of the accelerator of FIG. 2.

There are many types of mechanical systems which can be envisioned to accelerate biologically inert small carrier particles. Possible mechanisms might include ballistic explosive acceleration of particles, centrifugal acceleration of particles, electrostatic acceleration of particles or any other analogous system capable of providing momentum and velocity to small inert particles. Two novel mechanisms used by the applicants here are illustrated in schematic fashion in FIG. 1 and FIGS. 2-3. Each of these mechanisms illustrated here makes use of a shock wave created by high voltage electrical discharge. In FIG. 1, and generally indicated at 10, is one accelerator for accelerating the inert particles using this method. Shown in FIGS. 2-3 is a second accelerator, indicated at 110. In each figure, the target surface carrying the target cells is labelled 22.

The accelerator 10 consists of several parts. A spark discharge chamber 12 has provided extending into its interior a pair of electrodes 14. The geometry of the spark discharge chamber 12 is cylindrical. The applicants have found that a section of 13 millimeter interior diameter polyvinyl chloride plastic pipe is satisfactory for use as the spark discharge section 12. The electrodes 14 are extending oppositely into the interior, mounted approximately 5 millimeters below the top of the spark chamber 12. The electrodes 14 themselves are formed by threaded bolts extending into suitable threads formed in the interior sidewall surfaces of the spark chamber 12 wall itself. The ends of the threaded bolts forming the electrodes 14 are protected with an arc-resistant alloy obtained from high electric voltage relay contact points cut to a size of approximately 2 millimeters by 2 millimeters by 3 millimeters and soldered to the ends of the threaded bolts. The gap between the electrodes 14 can be adjusted by appropriately threading the bolts into or out of the spark chamber 12. The preferred gap for discharge voltage of approximately 15 kilovolts between the ends of the electrodes is between 1 and 1.5 millimeters. The method of fabricating and mounting the electrodes 14 themselves is clearly subject to wide variation, although it is preferred that the electrodes be highly durable and that the distance of the spark gap between the electrodes be readily adjustable.

A spacer ring 16 is provided above the spark chamber 12. The spacer ring 16 may be constructed out of the same PVC pipe as the spark chamber 12 itself and preferably be cut to a vertical length of 6 millimeters. In a fixed apparatus for transformations of a single crop species, the spacer ring 16 may be constructed merely as a vertical extension of the spark discharge chamber 12, although a removable and replacable spacer ring 16 allows adjustment of the distance from spark discharge to carrier sheet to be varied so that the force of particle acceleration can be varied by conditions or by species. The spacer ring 16 may be left open at the top if a large carrier sheet 18 is used, but may also advantageously have its top opening partially restricted by a suitable closure to form a rectangular opening approximately 9 by 13 millimeters. Placed atop the spacer 12 is a carrier sheet 18. The carrier sheet 18 is a planar, light sheet formed of suitable size to be placed resting atop the spacer ring 16. The carrier sheet 18 s formed of flexible biologically inert sheet material capable of carrying biologically inert small particles thereon. The carrier sheet 18 functions to transfer the force of a shock wave from a spark discharge into acceleration of the carrier particles. It has been found that the carrier sheet 18 may advantageously be formed from 1 mil or 0.5 mil plastic coated aluminized mylar, with the 0.5 mil sheets being preferred, since in practice they result in better penetration of the particles into the plant cells. As a general practice, the smaller the actual surface area of the carrier sheet 18, the better penetration is obtained by the carrier particles into the plant cells. This consideration regarding penetration is balanced by the need to have the carrier sheet of a size which is easy to handle and which provides an impact pattern over a large enough field to be able to impact large numbers of plant cells in the tissue being treated. A carrier sheet size of 18 by 18 millimeters has been found to provide a good size yielding good penetration in a desirable impact pattern of the particles onto the plant tissue target.

The carrier sheet also functions to arrange the pattern of the particles as they contact the target surface. A uniform pattern of particles is highly desirable to ensure that as many cells on the target as possible are impacted, in order to maximize the yield of transformants. Non-transformed cells may be at a competitive advantage with transformants which may be partially debilitated by the carrier particles. Therefore, it is desirous to reach as close to 100 percent penetration of the target cells as is possible, and a uniform layer and pattern of particles on a carrier sheet 18 aids this objective.

As to the carrier particles themselves, any high-density material which is biologically inert should be acceptable for use as the DNA carrier particles within the context of the present invention. Metallic materials are preferred, such as tungsten and gold, which have a density of 19 grams per cubic centimeter. Iridium might also be preferable, having a density of 22, but has not been used by the applicants because it is only easily available in a relatively coarse powder. Tungsten is also probably less desirable compared to gold because it tends to oxidize in air in the presence of even trace moisture. Such an oxidation layer on the carrier particles tends to bind the particles together causing severe increase in average particle size as the particles aggregate together. Particles which are clumped in irregular aggregations are less desirable for the practice of the present invention, since such aggregations will vary widely in their mass and size, thus leading to difficulty in obtaining regularly replicable results. Other non-metallic materials of high density may also be useful as particles. It has been found that gold is a preferred material for the particles within the present invention, since it has high density, is relatively inert to both biological materials and to oxidation, and is readily commercially available in the form of spheres having a diameter of 1 to 3 micrometers a size which has been found to be particularly well suited for practice of the present invention. Suitable DNA sequences may be applied to the gold particles and the gold particles may be applied to the carrier sheet in a manner which will be discussed in further detail below.

Located above the carrier sheet 18 is a retainer screen 20. The retainer screen 20 is a 100 mesh stainless steel screen physically mounted in a plastic holder approximately 20 millimeters above the top of the spacer ring 16. The retainer screen 20 functions to restrain the carrier sheet 18 so that it does not proceed to the target.

The target surface 22 is a planar sheet of material capable of suspending the target regenerable soybean tissues, such as embryonic axes, dissected meristems, cotyledons from immature embryos or cotyledonary nodes, or epicotyl segments, thereon. In practice, it has been found that an easily useable target is a petri dish 60 millimeters by 15 millimeters inverted over the top of the assembly holding the retainer screen. Spacing from the retaining screen 20 to the target cells on the target surface 22 is therefore preferably approximately 5-10 millimeters. Spacing greater than about 15 millimeters, under the conditions of voltage and pressure described below, leads to reduced penetration of carrier particles into the plant cells, while a spacing of less than about 5 millimeters results in crushed cells in the event that the retaining screen 20 deforms under the force of the blast.

Shown in FIGS. 2-3 is an alternative, and improved, embodiment of a particle accelerator 110. In the accelerator 110, there is a discharge chamber 112 into which two electrodes 114, extend. The electrodes 114 are simple threaded steel bolts, without alloy ends, with a gap of about 2 mm between them, which may be bridged by a water droplet 124 of about 6 microliters. The discharge chamber 112, itself is, however, significantly different in geometry from the discharge chamber 12. The discharge chamber 112 is divided by a shield 113 into two subchambers 115 and 117. The subchamber 115, into which the electrodes 114 extend, is where the electrical spark discharge actually takes place. The subchamber 115 has a removable access cover 119, and a bottom surface including a series of steps 121 and a deflector surface 123 angled, at about 20° from vertical, toward the subchamber 117. The subchamber 117 has its top covered by the carrier sheet 18, identical to that described in conjunction with the embodiment of FIG. 1, and has a bottom deflector surface 125, angled at about 45° from vertical, forming much of its bottom surface. A threaded bore 127 in the bottom of the accelerator 110 allows it to be secured by a threaded bolt 129 to a mounting plate 131. The retainer screen 20 and the target surface 22 are identical to those used in the accelerator 10 of FIG. 1, with the preferred spacing being about 20 mm between the top of subchamber 117 and the screen 20, the screen 20 being, in turn, about 5-10 mm from the target 22. Later experimentation revealed that the steps 121 and the deflector surface 125 are probably unnecessary and the discharge chamber 112 have its interior in a simple box-like shape.

The accelerator 110 operates in a fashion similar to the accelerator 10. The accelerator 110 is intended to minimize shock wave impact to the plant tissues being transformed. The shock wave from the discharge between the electrodes 114 is inertially confined and reflected by the access cover 119. The shield 113 directly shields the carrier sheet 18 and the target 22 from the direct blast or shock wave from the spark discharge. Instead, the blast wave from the discharge is reflected off of the 45° angle of the deflector surface 125 upward at the carrier sheet 18, thus providing a vertical impulse to the sheet 18 while shielding it from the direct shock wave. The preferred spacing from the top of the subchamber 117 to the retaining screen 20 is about 20 mm so that the carrier sheet 18 has an opportunity to amply accelerate.

Figure 4:
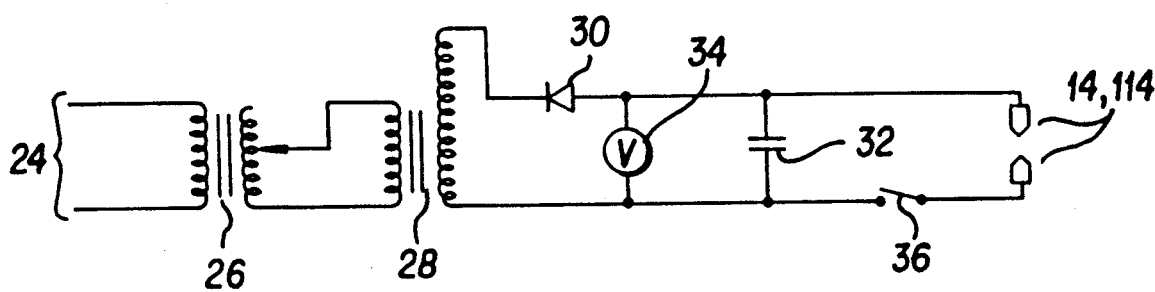
FIG. 4 is a circuit diagram of an electrical discharge circuit for use with the particle accelerators of FIGS. 1 and 2.

Shown in FIG. 4 is a circuit for use in creating an electrical discharge for either of the accelerators 10 or 110. Connected to AC power 24 is one coil of a variable transformer 26. The output of the variable transformer is connected to the input of a step-up high voltage transformer 28. The high voltage output of the transformer 28 is connected through a high-voltage silicon rectifier 30 to apply a DC-voltage to a high-voltage 2 microfarad capacitor 32. A voltmeter 34 is connected across the capacitor to monitor its voltage. A switch 36 connects the output of the capacitor 32 through the electrodes 14. The use of the variable transformer 26 allows the DC voltage which accumulates in the capacitor 32 to be adjusted as desired to vary the force of the blast between the electrodes 14 or 114.

When regenerable soybean tissue (including embryonic axes, excised or intact meristems, cotyledonary nodes, axillary buds, epicotyl segments, or similar tissues) is used as the target cells, the tissue must be physically secured to the target in such a fashion that the target may be inverted with the tissues being retained while also remaining viable. It has been found that using an agar-based medium with 8% xantham glue on the target surface is effective to hold the target tissue in place for the transformation.

For soybean tissues which are promptly transferred after treatment to a regeneration medium, a simple 1% to 5% water-agar medium may be used on the target surface. The agar formulation may then be plated in the bottom of small Petri dishes and allowed to harden. The tissues to be transformed may then be plated on the agar formulation, which will serve as the target surface.

The entire assembly of the particle accelerator 10, or 110, and the target surface 22 may be partially evacuated so as to prevent the force of atmospheric drag from slowing the particles and/or the carrier sheet 18. The vacuum should be only a partial vacuum since a high vacuum would desiccate the target plant tissues, rendering them non-viable. A vacuum of about 500 millimeters of mercury has been found sufficient and advantageous. Introduction of helium into the vacuum chamber also is advantageous because helium, being of low density, does not carry the shock wave from the electric discharge to as great an extent thus lessening shock wave damage to the plant tissues or the target. Since the particle accelerator 10 or 110 is assembled in air, then evacuated with helium introduced, air will be present in the discharge chamber 12 or 112 to efficiently carry the shock wave from the electric discharge to the carrier sheet 18, while helium will be present in the vacuum chamber. Placing a water film under the carrier sheet helps adhere it to the chamber so that air is retained in the discharge chamber 12 or 112.

In the simplest explanation of the operation apparatus of FIG. 1, the process of firing the accelerator 10 or 110 begins with the placement of a drop 24 or 124 of distilled or demineralized water between the electrodes 14 or 114. The amount of water must be selected so as not to dampen the arc which will occur between the electrodes but yet be of sufficient volume to create a shock wave in the interior of the spark chamber 12 or 112 when the discharge does occur. The preferred volume of water has been found to be approximately 2-6 microliters and is preferably about 6 microliters in the accelerator 110. This amount of water may be applied by pipette suspended between the ends of the electrodes 14 or 114. The water droplet 24 will bridge the gap between the electrodes and remain in place. It has been found helpful to coat the tips of the electrodes with a layer of lightweight oil before applying the water droplet 24 to lessen pitting of the electrodes and to increase the efficiency of the force of the electric discharge.

The carrier sheet 18 is then placed on the top of the spacer ring 16 or the top of the subchamber 115. The retaining screen 20 is mounted in place about 20 millimeters above the carrier sheet 18 and the target surface 22 consisting of the overturned Petri dish is placed above the mounting of the retaining screen 20. The assembly is then evacuated to about 500 millimeters of mercury.

The AC supply voltage is connected to the circuit of FIG. 4 to generate a high direct current voltage on the capacitor 32. The voltage may be varied somewhat, by adjustment of the variable transformer 26, depending on the tissue type and the spacing used. The variability of this voltage allows the force of the electric discharge, and thus the force applied to the carrier sheet 18, to be adjusted or tuned as needed for the species and tissue type of the target tissues. Voltages in the range of 10,000 to 30,000 volts have proved most successful in use with the apparatus of FIGS. 1-3. A high DC voltage is thus applied to the microfarad capacitor 32. By throwing the switch 36, the high voltage charge on the capacitor 32 is then applied between the electrodes 14 or 114.

When the voltage is applied, an electric discharge arc jumps between the two electrodes 14 or 114. The arc instantly vaporizes the small water drop 24 or 124 extending between the electrodes. A shock wave from the explosive vaporization of the water drop propagates throughout the interior of the spark chamber 12 or 112. When the shock wave reaches the carrier sheet 18, the carrier sheet 18 is lifted vertically off the accelerator and is accelerated toward the retaining screen 20. When the carrier sheet 18 hits the retaining screen 20, the carrier sheet 18 is restrained in place and the particles carried on the carrier sheet 18 leave the carrier sheet and fly freely across the distance to the cells resting on the target surface 22. If the apparatus has been properly constructed and adjusted, and the procedure properly followed, a significant percentage of the carrier particles will arrive at the target with a correct velocity to penetrate the cells carried on the target surface 22, without destroying an unacceptable percentage of the cells. This portion of the process thus yields a differentiated and regenerable plant tissue in which a significant number of the cells of the tissue have had inserted into them at least one particle carrying thereon the foreign DNA.

The tissues must then be regenerated into whole plants. If immature excised embryonic tissues are used as the target for the transformation process, the regeneration into whole plants may be accomplished by either of embryogenesis or organogenesis. Techniques for performing both of these procedures are known in the art. Barwhale et al., *Planta,* 167:473-481 (1986); Wright et al., *Plant Cell Reports,* 5:150-154 (1986). Excised meristems may also be readily regenerated by organogenesis through the same techniques. If the above agar formulation is used for the target surface, the tissues must be transferred to a separate culture plate to begin the regeneration procedure on an agar formulation which has been dosed with the correct hormones. A particularly advantageous target tissue has been found to be the excised embryonic axes dissected from mature or immature seeds. The entire intact embryonic axis may be used with or without a portion of cotyledonary tissue remaining thereon as long as the meristem is exposed as a target. Cultured meristems from such axes may be cultured to yield multiple shoots some or part of which may be partially or wholly transformed.

Regeneration of whole sexually mature plants will not end the procedure if the introduction of foreign genes into plant lines is the object, however. The plants which are regenerated in this fashion will typically be chimeric. While it is demonstrated here that the foreign genes will be passed to at least some of the progeny of the sexually mature plants, because of the chimerism only a portion of the progeny from the regenerated plant produced in this fashion will carry the transformant DNA. Therefore, the progeny of the regenerated plants may need to be screened or selected for inheritance of the foreign DNA. The screening for the foreign DNA may be done by hybridization assays for the DNA, by biochemical assays for the expression products, or by screening for plant phenotypes characteristic of the presence of the expression products of the introduced gene. The progeny which do carry the foreign DNA will then transmit the trait to their progeny through normal Mendellian inheritance. Initial experiments indicate that stable integration of introduced genes will occur with a much higher frequency than stable integration with expression of the desired foreign gene. Transient, or temporary, expression of the foreign gene is also quite commonly achieved. Thus, even though the gene constructions may express readily in soybean, many replications achieving stable integration may be required to achieve a stably expressing plant that will transmit the integrated gene to its progeny.

Within the preferred process of the present invention, the process for applying the DNA sequences to the particles, the process for layering the particles onto the carrier sheet, and the process for preparing the DNA for plant transformation all may require particular attention. Each of these details will be discussed in turn.

The DNA sequence including a foreign gene prepared in the form suitable for plant transformation can be simply dried onto naked gold or tungsten pellets. Other metallic materials, or alloys thereof, may also be used. The DNA may be loaded onto the particles at any rate up to (or over) 30 micrograms of DNA per milligram of gold bead spheres. The practice has been to add to 100 micrograms of DNA and 30 milligrams of 1-3 micron gold spheres sequentially 5 microliters of 10 mM $Na_2HPO_4$ and then 5 microliters of 10 mM $CaCl_2$ to provide a fine $CaHPO_4$ precipitate which forms as the solution dries. The precipitate carries the DNA with it onto the beads. It has been found useful to add EDTA to the suspension in some instances, for reasons not fully understood. Once the beads and the phosphate and calcium chloride solution have been mixed with the DNA, the suspension is dried under a nitrogen ($N_2$) stream with frequent stirring. Once dried, the pellet is immediately resuspended in 100% ethanol for the process of placing the particles onto the carrier sheet.

In applying the particles to the carrier sheet, it is preferred for the successful operation of this procedure to form a uniform and reproducible layer of the carrier particles on the carrier sheet. To do this, the particles cannot be simply dusted onto the carrier sheet, since they tend to aggregate and are thus distributed unevenly in a non-reproducible fashion on the sheet. In particular, moisture or water content on the sheet will disrupt the application of the particles to the sheet and result in undesirable aggregations. The carrier particles, with the precipitated coating containing the DNA strands, suspended in 100% ethanol, are then applied to the carrier sheet. A well stirred suspension of the ethanol with the carrier particles can be successfully pipetted onto the mylar sheet in a reasonably uniform and reproducible fashion. The pipetted aliquot of this suspension is then allowed to settle in a closed petri dish for at least 30 seconds. The petri dish must be closed to prevent eddy currents from forming from room air currents and from a high rate of evaporation, such eddy currents potentially causing excessive drifting of the particles and therefore a non-uniform distribution of particles on the sheet. After the settling period, the meniscus is broken and the excess ethanol is drained away. The residual ethanol is removed by evaporation in a partially opened petri dish.

This process is intended to place the carrier particles coated with the precipitate containing DNA strands on the mylar carrier sheet. A good median rate which is found successful within the present invention is approximately 0.1 milligram of carrier particles carrying the precipitate and DNA applied per square centimeter of the carrier sheet. Such a density of carrier particle application to the carrier sheet results in good survival of the treated tissues and also a high penetration of cells in the tissues by the accelerated particles. The actual acceleration and penetration of the cells by the particles will vary both with the tissue being treated, and the number of carrier particles can obviously be varied to give more or fewer particles per cross-sectional area of the target cells as desired.

The DNA for use within the present invention will normally be constructed in a vector appropriate for expression of the exogenous or foreign gene product in the cells of soybean, or whatever other plant is being utilized within the present invention. The DNA sequence can be chimeric, in the sense of being constructed from DNA sequences from different organisms but full intact non-chimeric genes from other plant species or lines of the same species may also be used. Vectors suitable for expression in plants generally must include, besides the coding sequence of the desired exogenous or foreign gene, appropriate flanking regulatory sequences such as a suitable promoter capable of promoting transcription and expression in vivo in plant cells, a transcription terminator capable of signalling the end of transcription, and a translation terminator suitable to terminate translation of messenger if protein synthesis is desired. Protein synthesis is not always required to condition phenotypic changes in plants. See EPO. Pat. Appl. No. 022399 to McCormick et al. It has been previously demonstrated that general plant gene promoters capable of causing coding sequence transcription and expression in model species are also effective in most plants. Fromm et al., *Proc. Natl. Acad. Sci. USA*, 82:5824–5828, September 1985. Such promoters include the nopaline synthase promoter from the plant pathogen *Agrobacterium tumefaciens* and the CaMV35s promoter derived from the cauliflower mosaic virus sequence. A suitable termination sequence effective in plants is the polyadenylation sequence from the nopaline synthase gene of *Agrobacterium tumefaciens*. The plant expression vector may also contain a selectable marker operative in plant cells to allow for selection of transformant plants. The selectable marker may condition a trait which may be assayed biochemically or a phenotypic trait which may be observed in the progeny plant. Clearly if a non-chimeric intact gene, with flanking regulatory sequences, from the same or another plant is used in the present process, chimeric promoter or control sequences are unnecessary and the gene may be used with its native sequence.

Since not all of the plant cells will have carrier particles inserted into them, and since not all plant cells or progeny cells will uptake the DNA into their genome, it may be desirable to screen the progeny plants at some stage to select for transformants. If it is desired to transform a given foreign gene into a plant, the gene may be inserted into a chimeric expression vector. The chimeric expression vector could then be transformed into plant cells along with a selectable marker plasmid, such as pCMC1022 described herein below. The two vectors (foreign gene and selectable marker) can be ligated together to make one plasmid, or the two vectors can be cloned separately and then applied together to the same carrier particles. In either event, the progeny produced are screened for the marker to select transformed progeny. While the use of such a selectable marker may be desirable in some circumstances, it may be omitted if a suitable morphological or biochemical test exists to screen for the transformed progeny. A morphological screening test could be for a dominant phenotypic trait in the progeny. A suitable biochemical screening test could be a so-called "Southern" blot hybridization for the existence of the transforming DNA itself in the genome of the progeny plants. If the frequency of plant transformations is high enough, as it is disclosed to be here, verification of the existence of the foreign gene in the transformed tissues can be practically performed by such a biochemical analysis, or by a probe for the presence of the gene itself, without the need for either a selectable or screenable marker.

Useful model genes to verify plant transformation and expression include the gene for aminoglycoside-3-phosphotransferase II (APH 3'II) (also known as neomycin phosphotransferase) and the beta-glucuronidase (gus) gene from *E. coli*. The APH 3'II gene conditions for resistance to aminoglycoside antibiotics such as kanamycin. The gus gene codes for the enzyme of that name which, in a tissue-destructive assay, will turn a substrate, indigo-glucoronide, or 5-bromo-4-chloro-3-indolyl glucuronide, blue in color in situ in plant tissues.

Numerous transformation experiments on soybean have demonstrated that non-expressing stable transformation can be achieved at a frequency much higher than the frequency of stable expressing transformation. Because no practical antibiotic resistance selection technique has yet been proven effective in soybean, biochemical assays, such as enzyme analysis or Southern blots, may be required to verify expression and transformation. Since the desired events may be low frequency, and the assay for the occurrence of these events relatively laborious, it becomes desirable to investigate techniques to increase significantly the frequency of expression in the transformed plants. One technique used here was first to create stably transformed soybean protoplasts, transformed either by electroporation or particle acceleration. This can be accomplished relatively expeditiously using the APH 3'II gene because of the large number of photoplasts which can be screened and because transformed soybean protoplasts can be selected for kanamycin resistance, a technique which has not yet proven effective in differentiated tissues. The stably transformed and expressing soybean protoplasts can then be induced to form callus cultures to multiply their tissue mass. Then the DNA from such a callus can be extracted, digested and transformed into regenerable soybean tissue. This technique has led to whole, stably transformed and expressing mature fertile soybean plants.

EXAMPLE 1

Construction of Vectors

A. Antibiotic Resistance

Figure 5:
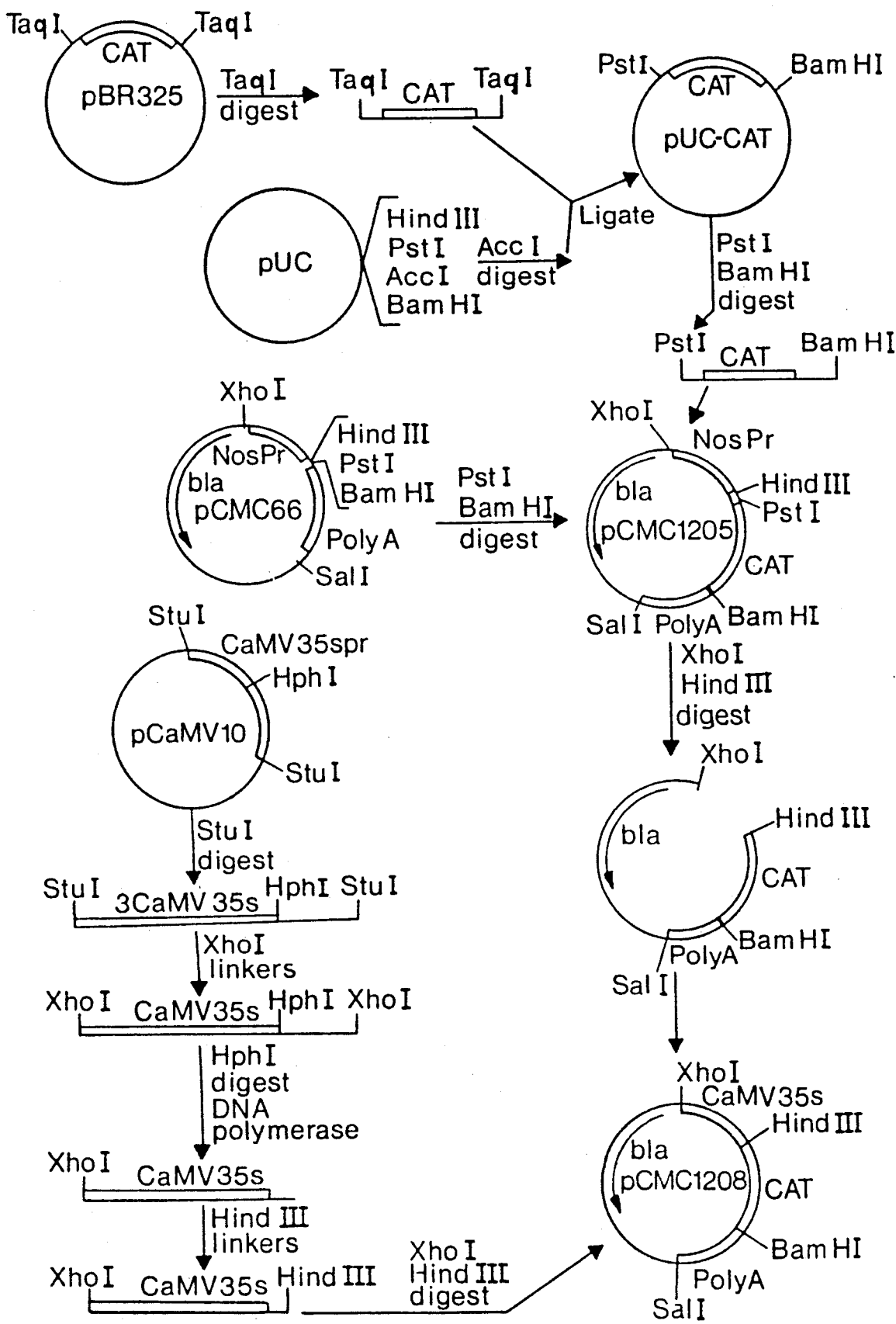
FIG. 5 is a schematic view of a series of plasmid manipulations for construction of the plant expression vector pCMC1208.
Figure 6:
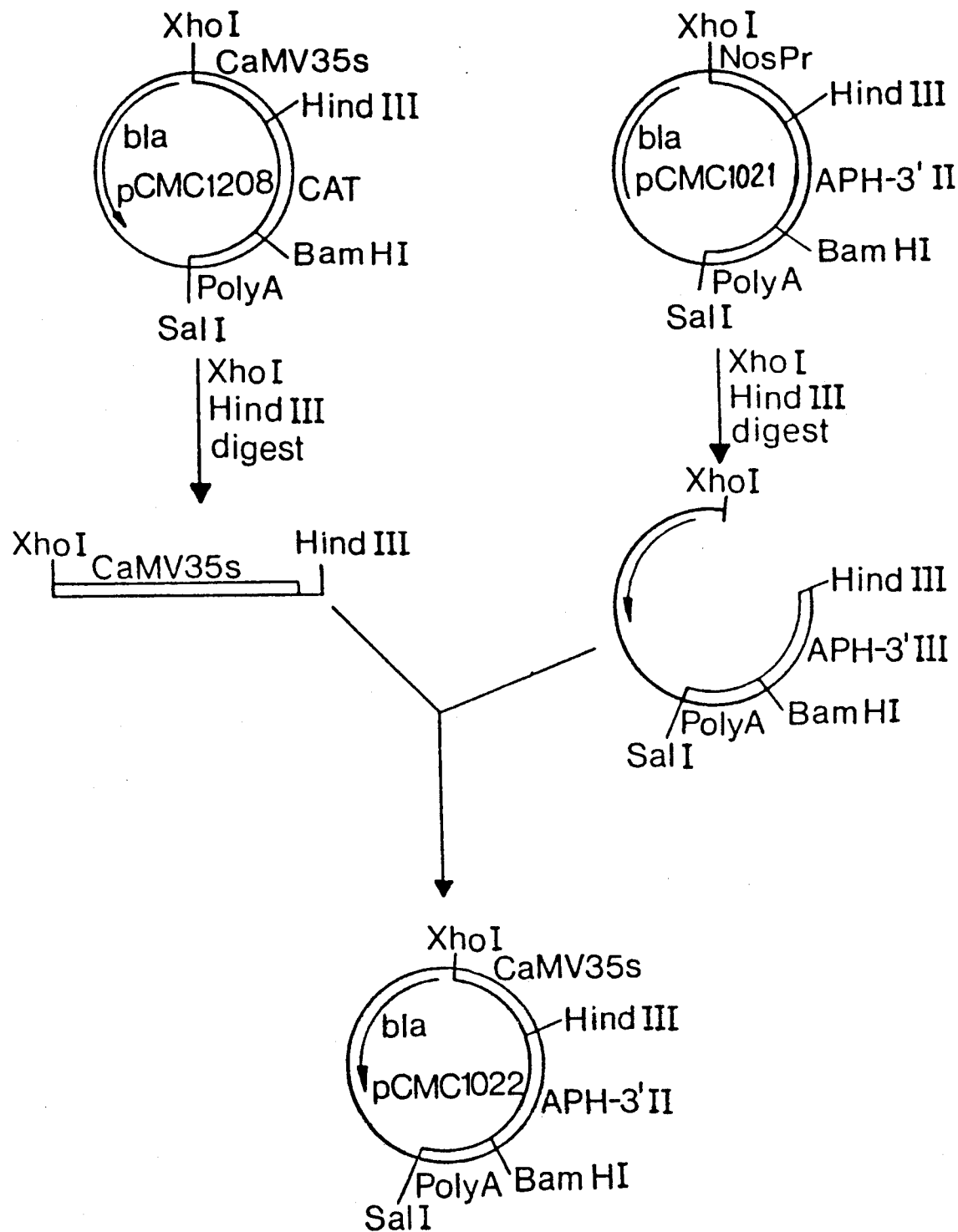
FIG. 6 is a schematic view of an additional series of plasmid manipulations for construction of the plant expression vector pCMC1022.

The construction of suitable plant expression vectors is illustrated in schematic fashion in FIGS. 5 and 6. FIG. 5 illustrates, in schematic form, the construction of a plant expression vector pCMC1208 and FIG. 6 illustrates the construction of vector pCMC1022. The construction of the plasmid pCMC1208 began with the digestion of the plasmid pBR325 (Bolivar, F. *Gene* 4:121–136 (1978)) with the restriction endonuclease Taq I. The plasmid pBR325 contains a coding sequence for the antibiotic resistance gene chloramphenicol acetyl transferase (CAT), which was excised from the remainder of the plasmid by Taq I digestion. After digestion of pBR325, the fragments were resolved by electrophoresis in an agarose gel and the fragment containing the CAT gene was excised. The CAT fragment was then ligated into the plasmid pUC9 (Viera & Messing, Gene, 19:259-268 (1982)) which had previously been digested with the restriction enzyme Acc I. The fragment ends produced by Taq I and Acc I are complementary in this case and thus the strands were directly ligatable. The resulting plasmid, designated pUC-CAT in FIG. 5, contained the CAT coding sequence flanked by portions of the polylinker from pUC9. This plasmid was digested with Pst I and BamH I, and the smaller of the two fragments was isolated by gel electrophoresis. This fragment was then ligated to an intermediate plant expression vector pCMC66, which had been previously digested with Pst I and BamH I, to form the CAT expression plasmid pCMC1205. The plasmid pCMC66 contains the nopaline synthase promoter (Nos Pr) from *Agrobacterium tumefaciens* and a nopaline synthase polyadenylation sequence (Poly A), from the same organism, surrounding six plasmid-unique restriction sites. The plasmid pCMC66 also carries a version of the beta-lactamase gene (bla) which expresses resistance to the antibiotic ampicillin in bacteria, so that ampicillin resistance can be used as a selection marker in subsequent recombinations performed in *E. coli.*

The plasmid pCaMV10 (Gardner et al., Nucl. Acids Res 9:2871-2888(1981)) was digested with Stu I and the fragment containing the cauliflower mosaic virus 35 promoter (CaMV35s) was joined to synthetic Xho I oligonucleotide linkers. The fragment was then digested with Hph I, treated with a DNA polymerase to generate blunt ends, and then joined to synthetic Hind III oligonucleotide linkers. Digestion of this fragment with both Xho I and Hind III produced a fragment containing the CaMV35s promoter and transcription start site modified at its ends by the addition of the restriction site sequences.

The nopaline synthase promoter was excised from pCMC1205 by digestion of the plasmid with Xho I and Hind III. The larger of the two fragments thus produced was ligated with the CaMV35s promoter fragment to produce pCMC1208, a plant expression vector having the CaMV35s promoter, the CAT coding sequence and the nopaline synthase polyadenylation sequence in order. The CaMV35s promoter and nopaline synthase poly A sequences served as the flanking regulatory sequences for the CAT coding sequence.

Both of the plasmids pCMC1205 and pCMC1208 were tested for activity in maize and soybean by electroporation into protoplasts, followed by an assay for CAT activity. Both constructions proved active in maize cells, but pCMC1208 proved significantly higher in level of activity, and thus was selected for plant transformation experiments. It was decided, however, that the selectable marker APH 3'II offered more promise for transformant selection, and thus pCMC1208 was not used for soybean cell transformation.

The plasmid pCMC1021 contains the nopaline synthase promoter and the nopaline synthase polyadenylation sequence flanking a coding region for the enzyme aminoglycoside-3-phosphotransferase II (APH 3'II) which conditions for resistance to aminoglycoside antibiotics such as kanamycin. Since electroporation experiments revealed the CaMV35s promoter to be much more effective in plant cells than the Nos Pr, it was decided to transfer the CaMV35s promoter to pCMC1021. The CaMV35s fragment from pCMC1208, as illustrated in FIG. 3, was isolated by digestion with Xho I and Hind III and isolation by electrophoresis. The plasmid pCMC1021 was also digested with Xho I and Hind III and the larger fragment isolated and ligated with the CaMV35s fragment to produce pCMC1022. In plasmid pCMC1022 the coding sequence from APH3'II is flanked by the regulatory CaMV35s and nopaline synthase poly A sequences.

The plasmid pCMC1022 was demonstrated to be effective for transformation and expression in individual cells of a variety of plant species, through electroporation transformation and protein assays. Plant cells transformed in culture with the APH 3'II have been demonstrated to be resistant to kanamycin for several species, including soybean.

B. Luciferase Marker

The presence of the enzyme luciferase in a biological sample may be detected by means of the characteristic luminescence of its reaction products. The gene coding for firefly luciferase is widely available and was supplied to the investigators here in plasmid pD0432, described by Ow et al., Science 234:856-859 (1986). This plasmid is a construct of the plasmid vector pUC19 containing a plant expressible chimeric gene consisting, in 5' to 3' sequence, of the 35s promoter of the cauliflower mosaic virus, an approximately 85 base pair sequence coding a segment of the firefly luciferase mRNA which is untranslated, the amino acid coding region of firefly luciferase, a region of firefly genomic DNA encoding a 3' untranslated mRNA, the polyadenylation sequence from the firefly luciferase gene, and a DNA sequence encoding the carboxyl-terminus and polyadenylation region of the nopaline synthase gene.

Figure 7:
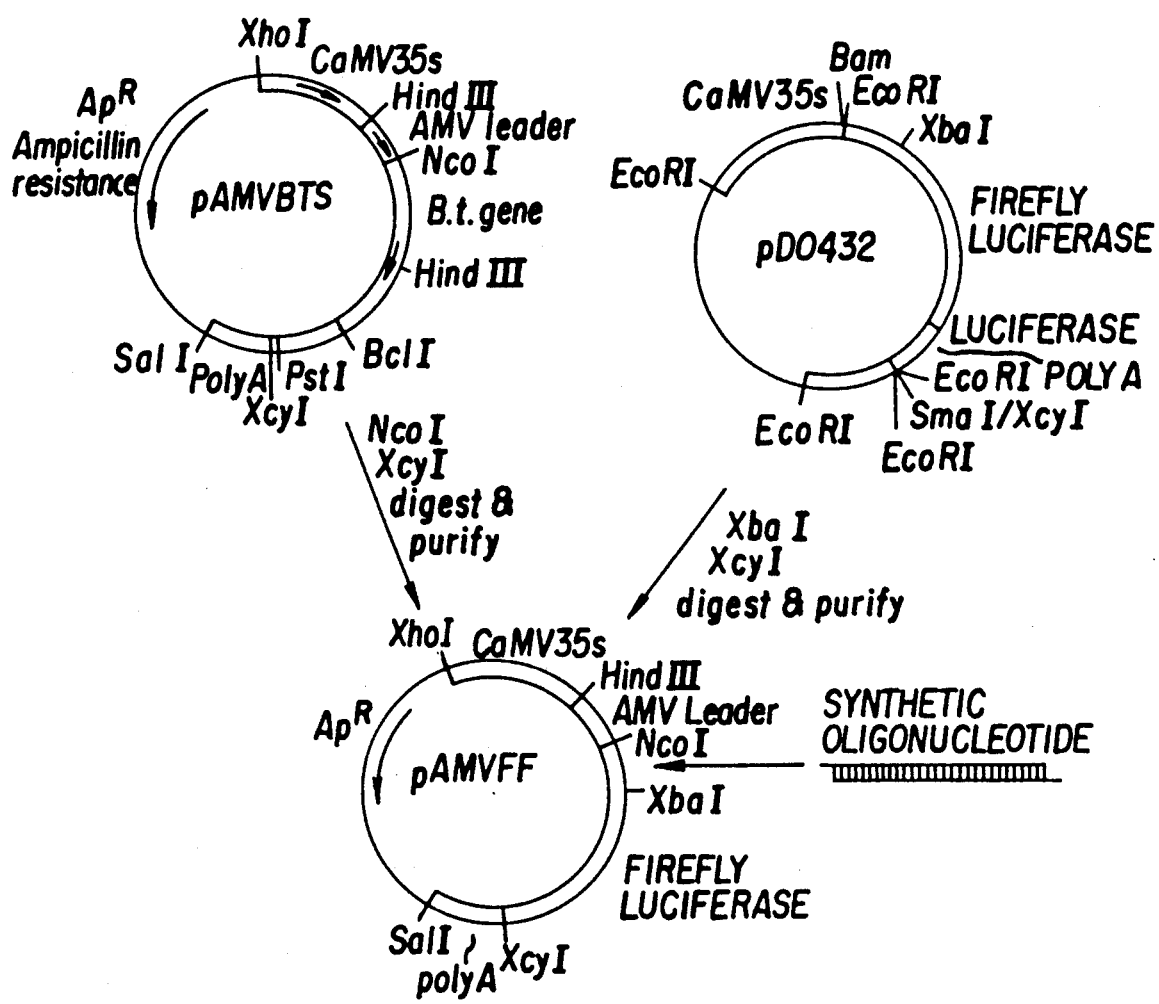
FIG. 7 is a schematic view of the plasmid manipulations necessary for the construction of the plant expression vector pAMVFF.

The other plasmid used in the method illustrated in FIG. 7 for creating the luciferase expression plasmid pAMVFF is the plasmid pAMVBTS. The plasmid pAMVBTS, deposited ATCC Accession No. 53637, contains a plant expressible chimeric gene including (in sequence 5' to 3') the 35s cauliflower mosaic virus promoter, a synthetic DNA fragment encoding the alfalfa mosaic virus (AMV) coat protein mRNA 5' untranslated region, a DNA fragment encoding an amino-terminal portion of the *Bacillus thuringiensis* delta-endotoxin, and a fragment encoding the polyadenylation region of the nopaline synthase gene from *Agrobacterium tumefaciens* strain A208.

The plasmid pAMVFF is constructed from three DNA fragments, (1) the vector from pAMVBTS without the toxin coding region, (2) a synthetic oligonucleotide corresponding to the amino-terminus of the firefly luciferase gene, and (3) the majority of the luciferase coding region from pD0432.

The plasmid pAMVBTS was digested with the restriction enzymes Nco I and Xcy I to separate the BT coding region from the vector. NcoI cut once on this plasmid between the alfalfa mosaic virus 5' leader and the initiation codon, (ATG), which is within the Nco I recognition sequence. Xcy I cuts at the same recognition site as Sma I, of which there is also only one site on this plasmid, at the junction between the terminus of the BT toxin coding region and the polyadenylation region. The digested DNA was resolved by agarose gel electrophoresis. The 2.5 kb vector was purified from the 1.8 kb BT toxin coding region by staining with ethidium bromide, excising the stained vector band, and electroelution. The result was a purified AMV-vector with Nco I and Xcy I sticky ends.

The plasmid pDO432 has an Xcy I (or Sma I) site after the firefly luciferase polyadenylation region, suitable for isolating the 3' end of the coding region. However, the initiation sequence was not accessible to NcoI digestion. The plasmid pDO432 was therefore digested with Xcy I and Xba I which cut 48 nucleotides from the amino-terminal end of the coding region. The 1761 base bair fragment was isolated by agarose gel electrophoresis, excised, and electroeluted.

The missing base pairs of the coding region were supplied by a synthetic oligonucleotide with NcoI and XbaI sticky ends. The synthetic duplex oligonucleotide was as follows:

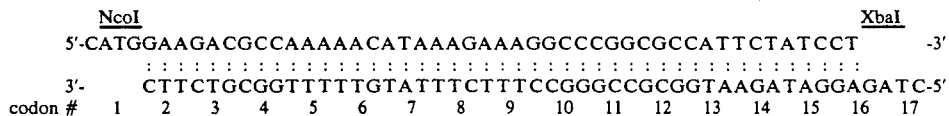

```
       NcoI                                                          XbaI
5'-CATGGAAGACGCCAAAAACATAAAGAAAGGCCCGGCGCCATTCTATCCT            -3'
   : : : : : : : : : : : : : : : : : : : : : : : : : : : : : : : : : : : : : : : :
3'-    CTTCTGCGGTTTTTGTATTTCTTTCCGGGCCGCGGTAAGATAGGAGATC-5'
codon #  1   2   3   4   5   6   7   8   9  10  11  12  13  14  15  16  17
```

The three fragments were combined in equimolar amounts and ligated. The ligation mix was transformed into E. coli strain MM294 and selected with ampicillin. Mapping of miniprep DNA with restriction enzymes and sequencing of the synthetic oligonucleotides confirmed the predicted sequence order.

The finished pAMVFF is an ampicillin resistant plasmid capable of replicating in E. coli, containing a plant expressible gene including, in 5' to 3' order, the transcriptional promoter of the 35s unit from CaMV, the synthetic DNA encoding the AMV 5' untranslated leader sequence, the complete coding region and polyadenylation region from firefly luciferase, and the polyadenylation region from the nopaline synthase gene from Agrobacterium.

C. Gus Gene

The plasmid pCMC1100 was constructed to direct the expression of the enzyme B-glucuronidase (or gus) in plant cells. The plant expression plasmid pCMC1100 was constructed from the plant expression vector pAMVBts, described above, and the vector pRAJ275. The gus gene is widely available and was supplied by Dr. Richard Jefferson in the form of plasmid pRAJ275. The plasmid contains a gus coding sequence modified to create a Nco I site (i.e. CCATGG) at the initiation codon (ATG) and includes a unique EcoR I site downstream of the gus coding region.

Figure 8:
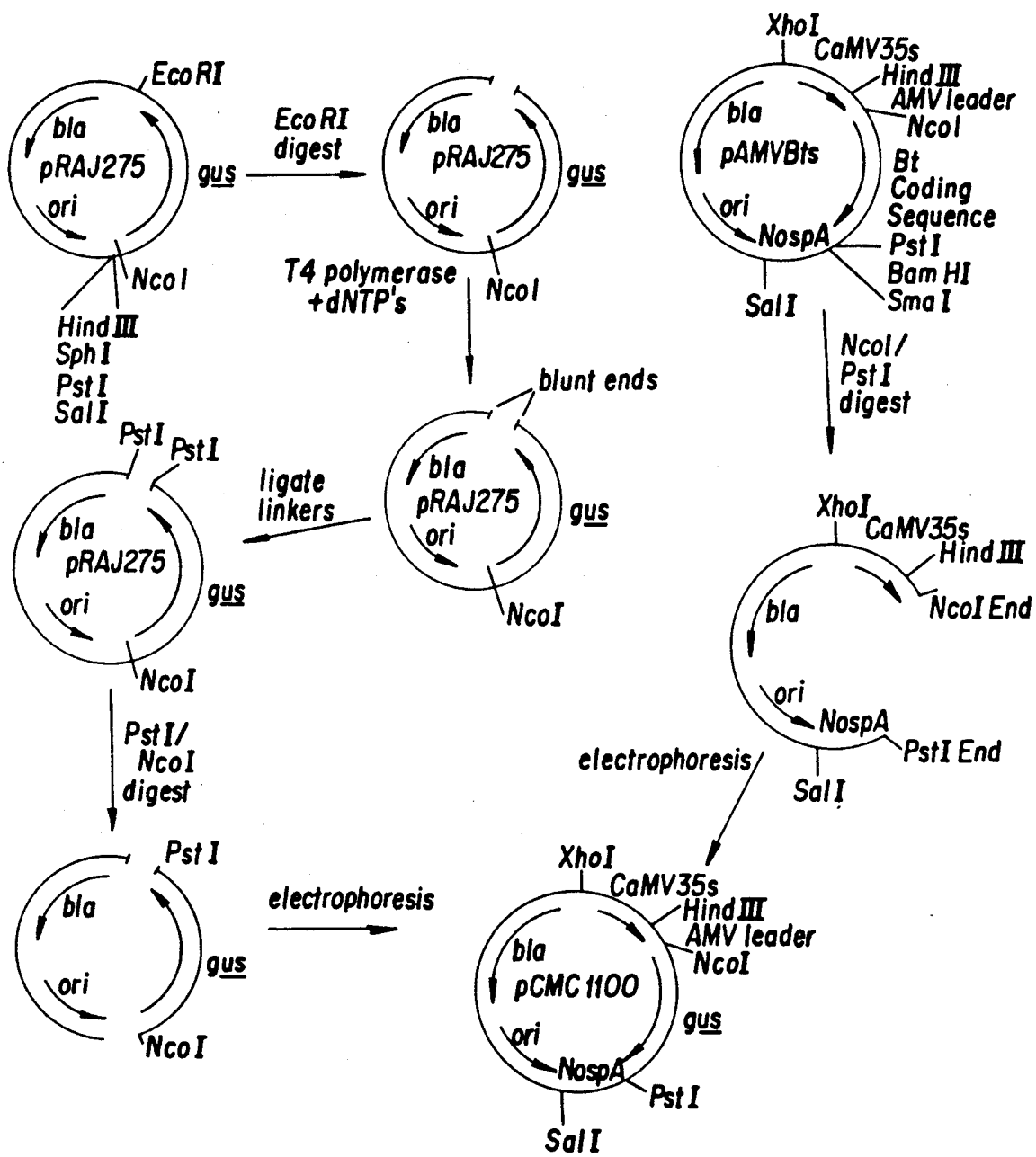
FIG. 8 is a schematic view of the manipulations necessary for the construction of the plant expression vector pCMC1100.

To prepare pCMC1100 from pRAJ275, as is illustrated in FIG. 8, plasmid pRAJ275 was digested with EcoR I and then the EcoR I sticky ends were blunt-ended by T4 DNA polymerase in the presence of all four dNTP's. Synthetic Pst I linkers were then ligated to the blunt ends of the DNA. The resulting molecule was then digested with Pst I and Nco I to completion and the fragment containing the gus coding region was separated by electrophoresis in an agarose gel.

Plasmid pAMVBts was prepared by digestion with Nco I and Pst I and the fragments resolved by electrophoresis in an agarose gel to purify the larger fragment. This fragment was then joined with the gus coding region fragment in the presence of T4 DNA ligase to produce pCMC1100. The resulting plasmids were transformed into E. coli and the structure of the correct plasmid confirmed by restriction mapping. The activity of the chimeric gus expression gene was verified by transient expression experiments in soybean and tobacco protoplasts. Samples of plasmid pCMC1100 have been deposited with the ATCC at accession No. 67641.

The presence of the gus gene can be assayed by colormetric and flourescence assays. For colormetric assay, the tissues or cells are first fixed by glutaraldehyde and then are soaked in a solution containing 1 mM x-gluc (Clontech labs), 0.1M NaHPO$_4$(pH 7.0), 0.5 mM potassium ferrocyanide. The tissue is then incubated for 24 hours at 37° C., cleared by boiling in lactophenol and examined for indigo blue deposits.

EXAMPLE 2

Transformation of Protoplasts

Four-to-eight millimeter zygotic embryos were excised from greenhouse grown soybean plants of varieties Williams 82, Mandarin Ottawa, and Hardin.

To create protoplasts, the embryos were chopped and plasmolysed and then incubated in a cellulase mixture for 4-5 hours at room temperature. The mixture was sieved through a 54 micrometer steel screen and the filtrate was washed and resuspended.

Tissues were bombarded with gold beads laden with pCMC1022 in the apparatus of FIG. 1. 70 micrograms of pCMC1022 (1 mg/ml in distilled water) was used to suspend 3.5 mg of 1-5 micrometer gold spheres (Alfa Chemical Co.) and dried under an N$_2$ stream. The dried coated beads were resuspended in 100% Ethanol. 162 microliter of gold/DNA suspension was plated on 18 mm × 18 mm of ½ mil saran coated aluminized mylar. Final gold concentration was 0.05 to 0.1 mg/cm$^2$. The spacer 16 used was 15 mm tall with the screen 20 located 5 mm above it. The target was an array of embryos on a 1% water agar petri dish inverted over the screen. The assembly was evacuated to 500 mm of mercury before discharge.

Embryos were bombarded and then protoplasted in some replicates. Embryos were partially protoplasted and then bombarded in others. In either case, the resulting protoplasts were examined for presence of the gold particles and were plated on a kanamycin selection medium (50 mg/l kanamycin). Kanamycin resistant colonies initially appeared in 2-3 weeks and continued to appear for 6-8 weeks. Tissues were amplified until sufficient for enzyme and gene hybridization assays.

Enzyme activity and foreign gene (APH 3'II) presence were confirmed in all colonies, although the level of enzyme expression varied over five-fold. Microscopic examination of protoplasts derived from partially protoplasted tissue which was blasted revealed approximately 1 out of 10$^3$ protoplasts contained gold beads. For tissues bombarded as embryos and then protoplasted, about five protoplasts per thousand contained one or more gold particles. For protoplasts transformed by either method, approximately 1 out of 10$^5$ protoplasts resulted in a stably transformed kanamycin resistant callus.

EXAMPLE 3

Transforming Zygotic Embryos

A quantity of 1-3 micrometer gold spherical beads for use as carrier particles were pre-coated with polylysine by being rinsed in 0.02% polylysine and air drying. 225 micrograms of pCMC1022 DNA, linearized by digestion with PvuI, in aqueous solution had added to it 35 mg coated gold beads, and then sequentially 22 microliters of 10 mM $Na_2HPO_4$ and 22 microliters of 10 mM $CaCl_2$ which formed a fine precipitate as the solution was dried in a $N_2$ stream. The dried precipitate-coated beads were then re-suspended in 100% ethanol and deposited onto 2.0 mil plastic coated aluminized mylar sheets approximately 9 mm by 11 mm. The coated beads were applied to give a final density of 0.2 $mg/cm^2$ on the mylar carrier sheet.

The carrier sheet carrying the coated beads thereon was mounted atop the spacer 16 in the apparatus of FIG. 2. Soybean tissues from isolated zygotic embryos of varieties Mandarin Ottawa, Williams and Hardin were excised from immature soybean pods 15-25 days after pollination. The bottom of a 60 mm Petri dish was filled with 1% water agar formulation. The embryos were surface sterilized and plated onto the agar in the Petri dish. The Petri dish was used as the target surface 22 in the apparatus of FIG. 2.

A vacuum of 500 mm of Hg was applied to the assembled apparatus. A 24 kV discharge from the 2 microfarad capacitor was discharged through the electrodes 114 accelerating the coated particles at the soybean embryo on the target surface 22.

The process of preparing beads and embryos and firing the apparatus of FIG. 2 was repeated several times until an adequate supply of treated embryos was accumulated. The embryos were removed from the agar surface and plated onto plates for organogenesis procedures. The technique used was that described by Barwhale et al., *Planta*, 176:473-481 (1986). No selection pressure was used.

The plantlets produced in this fashion were segregated into four groups, each having about 25 plants. Plants in two of the groups were assayed for APH-3'II activity. The plants in each of these two groups were sacrificed and the tissues of all of the plants were pooled to obtain sufficient tissues for the assay. Weak positive APH-3'II signals were detected in both groups of the pooled samples, indicating that at least some of the plantlets were transformed and expressing the introduced DNA.

The presence of pCMC1022 sequences in the DNA isolated from these two groups of plantlets was assayed one month later by the Southern hybridization-technique. Southern, *J. Mol. Bio.*, 98:503-577 (1975). DNA was isolated from control and test soybean tissue samples by micromodification of the cetyl-trimethylammonium bromide procedure of Taylor and Powell, *Focus*, 4:4-6 (1982). 10 micrograms of each DNA sample was digested with the restriction enzyme Ava I, resolved by electrophoresis in an agarose gel, transferred to a nylon membrane, and hybridized with a $^{32}P$-labeled probe corresponding to the non-coding strand of the APH-3'II coding region. After washing the filter, hybridizing DNA fragments were visualized by autoradiography. Plants from both of the groups of plants were shown to carry the pCMC1022 DNA. Both groups of plantlets exhibited Southern blot bands indicating similar size fragments, although the intensity of the bands did vary between the two groups. Control tissues which were not subjected to the accelerated particles showed no APH-3'II activity and no corresponding bands in the Southern blot.

EXAMPLE 4

Regeneration by Embryogenesis

The above procedure has been repeated with both the APH-3'II expression plasmid pCMC1022 linearized by Pvu I and the circular luciferase expression plasmid pAMVFF. For this replicate the excised zygotic embryos were pre-incubated on somatic embryogenesis medium as described in Ranch et al., *In Vitro Cellular and Developmental Biology*, 21:11, 653-658 (1985) prior to the transformation process. The accelerator 110 was used with a 13 kV discharge. The DNA was loaded onto the gold at 10 micrograms, 0.1 microgram and 0.0001 microgram per milligram gold. The 1 mil carrier was loaded with 0.05 milligram beads (with DNA) per square centimeter. The plants were regenerated through both embryogenesis and organogenesis. The DNA was extracted from the resultant whole plants transformed with pCMC1022 and analyzed by Southern blot which demonstrated the presence and integration of the foreign DNA into the plant genome.

EXAMPLE 5

Transformation with Luciferase

Fifty embryonic axes were dissected from zygotic embryos and subjected to particle-mediated transformation using the luciferase expression plasmid pAMVFF in the method described in Example 2 above. Plantlets were regenerated by organogenesis and assayed destructively for luciferase activity. The activity of the luciferase enzyme could be detected in the transformed tissues using a luminometer.

EXAMPLE 6

Transformation of Embryonic Meristems

Soybean explants of cultivar Williams 82 were derived from meristems excised from the embryonic axes of immature seeds. Primary leaves were removed and the explant plated on a target plate containing 1% water agar.

The explants were transformed as in Example 3 with pCMC1100 DNA loaded at 1.0 to 0.001 micrograms per milligram of beads. The particle accelerator was charged at 13-16 kV. The carrier was loaded with 0.05 to 0.40 milligrams of loaded beads per square centimeter. The preferred level of loading was 0.2 milligrams per square centimeter.

The explants were then plated in the dark on the MS basal medium as modified by Barwhale et al., *Planta*, 167, 473-481 (1986), which has a high level, i.e. 13.3 micromolar, of the cytokinin benzylaminopurine. Following incubation of 1 to 2 weeks in the dark, the tissues were transferred onto the same basal medium at a lower (1.7 micromolar) level of cytokinin to promote shoot elongation. Shoots were harvested at 0.5 to 1 cm in height. Three to eight shoots were recovered per explant within 2-4 months.

The relative success of the transformation protocol was verified by fixing transformed explants at each stage to assay for gus activity. Two days after DNA particle injection, typically dozens of gus active cells could be detected in each explant. Many gus expressing cells, however, failed to divide or confer the trait to daughter cells. At 6 to 8 weeks, the plants could be assayed for gus activity in the shoot. Approximately one plant per 100 assayed positive, having at least one streak of blue, indicating gus activity. Most plants were chimeric, having streaks of blue (i.e. gus) tissues and other sectors of non-transformed or non-expressing tissue.

EXAMPLE 7

Transformation of Embryonic Meristems

Soybean explants of variety Williams 82 were generated by removing the immature embryos from immature seeds. The embryonic axes were plated and transformed by particle acceleration as in Example 6 above utilizing a plasmid pAcX1100.

Plasmid pAcX1100 was constructed by first digesting pCMC1100 with Xho I and Sal I to completion and isolating the fragment containing the chimeric gus expression gene. That fragment was then ligated into the Xho I site on pAc3. Plasmid pAc3 is an independent isolate of the Ac transposon supplied by N. Federoff and presumed to be identical to the plasmid pAc9 as described in Federoff, et al., *Cell*, 35:235-242 (1983). The plasmid pAc3 includes a complete copy of an active Ac element isolated from maize, in an *E. coli* vector which is selectable by its trait of tetracycline resistance. The Xho I site in pAc3 is inside the Ac element. The ligation of the gus gene construction into pAc3 was performed by a T4-DNA ligase catalyzed reaction. Activity of the resulting plasmid, designated pAcX1100 was confirmed by particle-mediated transformation into maize and soybean callus with subsequent assay for gus activity.

In this transformation experiment DNA of both plasmids pAc3 and pAcX1100 were loaded onto gold beads at a density of 0.01 microgram per milligram. 0.1 microgram of each plasmid was added to 10 milligrams of gold beads, then two microliters of 0.2M EDTA was added before drying under $N_2$. The dried beads were then resuspended in Ethanol and accelerated into the meristems plated embryos. The early shoots arising from the resultant meristems plated in high cytokinin medium were destructively assayed for gus activity. Out of twenty such shoots, one was entirely blue, indicating gus expression in all its tissues. This shoot therefore seemed to be totally transformed and not chimeric.

EXAMPLE 8

Transformation of Mature Seedlings

Seeds of soybean variety Williams was soaked for 24 hours in sterile distilled water to which had been added Carbennicillin (0.4 g/l), Cefotaxime (0.1 g/l), Bravo (0.1 g/l), Benomyl (0.1 g/l), Maneb (0.1 g/l) and Captan (0.1 g/l). The seed coat and one cotyledon were then removed to expose the embryonic axes which was left attached to the remaining cotyledon. The exposed ligules and primary leaves were dissected away and a large portion of the remaining cotyledon (approx. 75%) removed. The tissues were then mounted on a target plate, with the meristem facing upward, using a glue of 8% Xanthan gum in distilled water.

The tissues were transformed by particle acceleration with pCMC1100 loaded on gold beads at the rate of one microgram DNA to 10 milligram beads and the coated beads loaded on the carrier at 0.1 mg/cm².

Following particle injection, the dissected seedlings were allowed to germinate under sterile conditions for three days and then were planted in a greenhouse. Twenty-four days after particle injection, the seedlings were destructively assayed for gus activity.

Several seedlings were found to have sectors of gus expression as indicated by indigo color in cells of portions of the plant. The most common observance is a sector between nodes in a stem which terminates at each end node, but expressing leaf sectors were also found. All expressing plants appeared to be chimeric. By "chimeric" as applied to plants, what is meant is that some cells and tissues were genetically different from other cells and tissues in the same plant, as indicated by expression of the foreign gene. This example indicates that the transformed meristematic cells in a mature seedling can be used as a transformation target. The seedling which thus has its meristem transformed, can be cultivated by more conventional plant husbandry into a mature, though chimeric, plant.

EXAMPLE 9

Transformation of Meristem and Transmission to Progeny

Transformed and expressing soybean protoplasts of variety Mandarin were obtained as detailed in Example 2 above using pCMC1022. Callus cultures were derived on kanamycin giving APH 3'-II expressing tissues in some quantity. The tissues were disrupted and the DNA from the callus cells was recovered.

About 10 micrograms of DNA from each of six different stably transformed callus cultures was obtained. This total genomic DNA from each callus line was digested to completion with BamH I to size fraction the DNA. The completion of the digest was confirmed by a minigel. The restriction enzyme BamH I was selected since there are no BamH I sites in pCMC1022. The samples were then extracted with phenol:chloroform, precipitated with ammonium acetate and ethanol (twice) and size fractionated on a 0.8% agarose electrophoresis gel. The ethidium bromide stained gel was then cut into pieces according to size determined by a control lane. Two fractions, one of 3.5 to 10 kilobase and the other of 10 to 23 kilobase, were collected and the DNA was eluted from the gel by electroelution. Each sample was then purified to remove agarose by organic extractions. After two precipitations with ammonium acetate and ethanol the DNA was prepared for particle mediated transformation.

Soybean meristem explants were derived and transformed by DNA coated particle acceleration as in Example 7.

The meristems were pre-incubated on the high cytokinin-containing medium (Barwhale et al., supra) overnight prior to transformation. Primary leaves were removed.

The putatively transformed meristems were plated on the high cytokinin basal medium in the dark for 1 to 2 weeks. They were then transferred to the lower cytokinin medium and incubated under light (16 hour photoperiod). Multiple shoots resulted from each meristem. No selection for kanamycin resistance was made.

After the shoots reach 0.5-1.0 cm in height, they were grafted onto the roots of germinating approximately ten days old soybean seedlings. Prior to grafting they were hardened on ½ MS medium for one week. As soon as sufficient plant tissue was achieved, the tissues were assayed destructively for APH 3'-II activity. Two plants out of fifty exhibited APH 3'-II activity. Southern blot analysis indicated a copy number of less than one gene per cell, suggesting that each of the two plants were chimeric.

One plant, tissues of which had assayed positive for APH 3'-II, was successfully grown to maturity. The plant self-pollinated and thirty-seven seeds were recovered. Three out of ten seedlings derived from these seeds had APH 3'-II activity. Two of the seedlings produced from the seeds failed to develop into plants. One morphologically normal progeny plant was produced. Its leaf tissues continued to assay positive for APH 3'-II. Southern blot analysis indicated several copies of the APH 3'-II coding region in the genome of the plant.

This result verifies that stably transformed and expressing soybean plants ca be achieved by particle-mediated transformation of meristematic tissue. The fact that the regenerated plant is chimeric is not a bar to obtaining transformation of the plant germ line, as long as the plant is fertile and its self-pollinated progeny can be screened for presence of the introduced exogenous gene. Of course, a non-chimeric regenerated plant would also be expected to yield transgenic progeny.

EXAMPLE 10

Transformation of Embryonic Meristems

Soybean explants of variety Williams 82 were isolated by again excising the immature embryos from immature seeds. Again the embryonic axes were plated and transformed by particle acceleration as in Example 8 above, this time with plasmid pTVGUS. For this experiment the DNA was combined at the rate of 0.1 microgram DNA to 10 milligram gold beads with 2 microliter EDTA and 1 microliter 50% glycerine before being dried under $N_2$.

Plasmid pTVGus created by first linearizing the plasmid pCMC1100 by digestion with Xho I. The entire linear plasmid was then ligated into the Xho I site of plasmid pTV4, a chimeric plant expression vector constructed for Agrobacterium-mediated plant transformations and including a chimeric APH 3'II gene construction located between synthetic Agrobacterium T-DNA left border and right border regions. The plasmid resulting from this ligation, designated pTVGus, includes gene constructions for expression of both APH 3'II and gus.

Fifty shoots were recovered, grafted as in Example 8, and reached mature plant size with normal morphology. All fifty plants were assayed for APH 3'II and gus activity. One plant assayed positive. Leaf disk assays of the plant revealed both expressing and non-expressing tissues in the plant indicating the expected chimerism. The plant will be selfed and the seed recovered, some of which will be expected to give rise to transformed plants.

EXAMPLE 11

Use of pCMC1022 with Other Genes

To transform other genes of interest into soybean or other plants, plasmid pCMC1022 may be used in any of several ways. The APH 3'II coding sequence can be deleted by digestion of pCMC1022 with Hind III and Bam HI and another gene sequence of interest prepared with appropriate ends can be ligated in its place. If the gene of interest can reasonably be selected for or detected by convenient assay, the plasmid may then be directly used for transformations. If the gene of interest is separately prepared with appropriate regulatory sequences, and a detectable marker is desired, the gene of interest with its regulatory sequences can be inserted in any of the sites in the polylinker upstream of the CAMV35s sequence in pCMC1022. Another alternative to make use of the pCMC1022 detectable marker is to prepare the gene of interest, in pCMC1022 or in any other plant expression vector, and to coat pCMC1022 and the gene expression vector together onto carrier particles as disclosed herein for transformation into plant cells.

The DNA thus prepared can be used directly for transformation of excised meristems, or can be prepared by transformation first into protoplasts and recovered therefrom. The DNA can then be inserted into meristematic tissues by particle acceleration through the methods disclosed above. A fully mature, sexually mature, although perhaps chimeric, plant can then be grown from the transformed meristem tissues either by regeneration for excised meristems or by cultivation for mature meristematic tissues or seedlings. In any event, the possibly chimeric plants produced from the transformation can then be self-pollinated to produce transgenic non-chimeric progeny capable of passing the exogenous trait of the foreign gene by Mendellian inheritance. As illustrated, the method is independent of the particular foreign gene, and of the cultivar, thus overcoming some of the problems inherent in Agrobacterium-mediated plant transformation.

In any transformation experiment, a detectable marker may be transformed into the plant with the gene of interest. As disclosed here, gene constructions for the expression of APH 3'II, firefly luciferase, and gus, all express and are functional in cells of transgenic soybean plants. Thus by constructing a tandem construction of a new gene of interest with one of these detectable, or other, detectable markers, the detection of the occurrence of stably transformed plants and progeny can be achieved by detection of the marker. Because the transformation frequency appears sufficiently high that practical use of one of these detectable marker screenings is possible to detect transformants, a selectable marker, though perhaps desirable, is not required to achieve transformed plants.

The following plasmids were deposited both with the American Type Culture Collection, 12301 Parklawn Drive, Rockville, Md., U.S.A., and with the Cetus Master Culture Collection, Emeryville, Calif., under the following accession numbers:

| Plasmid | ATCC Accession No. | ATCC Deposit Date | CMCC Accession No. |
|---|---|---|---|
| pCMC1022 | 67269 | Nov. 14, 1986 | 2902 |
| pAMVFF | 67451 | June 24, 1987 | 3137 |
| pCMC1100 | 67641 | March 1, 1988 | 3290 |
| pAcX1100 | | | |

The above deposit was made pursuant to a contract between the ATCC and the Cetus Corporation, a partner in the assignee of the present invention. The contract with the ATCC provides for permanent availability of the progeny of these cell lines to the public on the issuance of the US patent describing and identifying the deposit or the publication or laying open to the public of any US or foreign patent application, whichever comes first, and for availability of the progeny of these cell lines to one determined by the U.S. Commissioner of Patents and Trademarks to be entitled thereto according to 35 USC Section 122 and the Commissioner's rules pursuant thereto (including 37 CFR Section 1.14 with particular reference to 886 O.G. 638). The assignee of the present application bas agreed that if the cell lines on deposit should die or be lost or destroyed when cultivated under suitable conditions, they will be promptly replaced on notification with a viable culture of the same cell line.

The present invention is not to be limited in scope by the microorganisms deposited, since the deposited embodiment is intended as a single illustration of one aspect of the invention and any microorganisms which are functionally equivalent are within the scope of this invention. Indeed various modifications of the invention in addition to those shown and described herein will become apparent to those skilled in the art from the foregoing description and fall within the scope of the appended claims.

It is also to be understood that all base pair sizes given for nucleotides are approximate and are used for purpose of description.

What is claimed is:

1. A method of making a genetically transformed soybean plant comprising the steps of:
   preparing copies of a foreign gene including a coding region and flanking regulatory sequences effective to express the coding region in soybean cells;
   joining copies of the foreign gene to biologically inert carrier particles;
   placing an embryonic axis from a soybean seed on a target surface;
   physically accelerating the particles carrying the foreign gene copies at the target surface in such a fashion that some particles lodge in the interior of at least some of the cells of the soybean embryonic acid;
   inducing shoot formation directly from the embryonic axis by hormone treatment without intermediate proliferation of tissue in callus culture;
   cultivating the shoot into a whole sexually mature soybean plant; and
   verifying the existence of the foreign gene in the tissues of the regenerated plant.

2. A method as claimed in claim 1 wherein the biologically inert particles are metallic.

3. A method as claimed in claim 2 wherein the metallic particles are gold spheres.

4. A method as claimed in claim 1 wherein the embryonic axis is from an excised zygotic embryo.

5. A method as claimed in claim 1 wherein the foreign gene is prepared as a plasmid hosted in a bacteria.

6. A method as claimed in claim 5 wherein the plasmid is pCMC1022 having ATCC accession number 67269.

7. A method as claimed in claim 5 wherein the plasmid is pCMC1100 having ATCC accession number 67641.

8. A method as claimed in claim 1 wherein the embryonic axis is placed on a target surface by plating such an excised tissue on a bed of an agar medium.

9. A method as claimed in claim 1 wherein the verifying the presence of the foreign gene is done by a hybridization assay for the presence of the foreign DNA itself.

10. A method as claimed in claim 1 wherein the verifying the presence of the foreign gene is done by an assay for the expression product of the foreign gene.

11. A method as claimed in claim 1 wherein the hormone treatment includes cultivation on a cytokinin containing medium to induce shoot formation.

12. A method as claimed in claim 1 wherein the step of cultivating the shoot into a whole plant includes the step of grafting the shoot onto a germinating soybean rootstock.

13. A method as claimed in claim 1 wherein the step of physically accelerating the particles carrying the foreign gene at the target surface includes placing the carrier particles on a planar carrier sheet, accelerating the carrier sheet with a shock wave, and stopping the carrier sheet while permitting the carrier particles to travel on toward the target surface.

14. A method as claimed in claim 13 wherein the carrier sheet is formed of aluminized mylar.

15. A method of making a genetically transformed line of soybean plants comprising the steps of:
   preparing copies of a foreign gene including a coding region and flanking regulatory sequences effective to express the coding region in soybean cells;
   joining copies of the foreign gene to substantially biologically inert carrier particles;
   placing a meristematic soybean tissue comprising the embryonic axis from a soybean seed on a target surface;
   physically accelerating the particles carrying the foreign gene copies at the target in such a fashion that some particles lodge in the interior of at least some of the cells of the embryonic axis;
   inducing by hormone treatment shoot formation directly from the embryonic axis without intermediate callus cultivation of the tissue;
   cultivating the shoot into a whole sexually mature regenerated plant;
   obtaining self-pollinated seed from the sexually mature regenerated plant;
   growing up progeny plants from the seed; and
   verifying the existence of the foreign gene in the tissues of at least some of the progeny plants.

16. A method as claimed in claim 15 wherein the biologically inert particles are metallic.

17. A method as claimed in claim 15 wherein the metallic particles are gold.

18. A method as claimed in claim 15 wherein the meristematic soybean tissue is an excised zygotic embryo.

19. A method as claimed in claim 15 wherein the meristematic soybean tissue is placed on a target surface by plating such an excised tissue on a bed of an agar medium.

20. A method as claimed in claim 15 wherein the verifying the presence of the foreign gene is done by a hybridization assay for the presence of the foreign DNA itself.

21. A method as claimed in claim 15 wherein the verifying the presence of the foreign gene is done by an assay for the expression product of the foreign gene.

22. A method as claimed in claim 15 wherein the hormone treatment includes cultivation of a cytokinin containing medium to induce shoot formation.

23. A method as claimed in claim 15 wherein the step of cultivating the shoots into whole plants includes the step of grafting the shoots onto a germinating soybean rootstock.

24. A method of making a genetically transformed line of soybean plants comprising the steps of:

preparing copies of a genetic construction including both a foreign gene and a marker gene, both genes including a coding region and flanking regulatory sequences effective to express the coding region of the gene in soybean cells;

joining copies of the genetic construction to substantially biologically inert carrier particles;

placing a plurality of embryonic axes from soybean seeds on a target surface;

physically accelerating the particles carrying the foreign gene copies at the target in such a fashion that some particles lodge in the interior of at least some of the cells of the embryonic axes;

inducing by hormone treatment shoot formation directly from the embryonic axes without intermediate callus cultivation of the tissue and without cell selection;

screening the shoots for expression of the marker gene;

cultivating the shoots expressing the marker gene into whole sexually mature regenerated plants;

obtaining self-pollinated seed from the secularly mature regenerated plants;

growing up progeny plants from the seeds; and verifying the existence of the genetic construction in the tissue of at least some of the progeny plants.

* * * * *

UNITED STATES PATENT AND TRADEMARK OFFICE
CERTIFICATE OF CORRECTION

PATENT NO. : 5,015,580
DATED : May 14, 1991
INVENTOR(S) : Christou et al.

It is certified that error appears in the above-identified patent and that said Letters Patent is hereby corrected as shown below:

Title page,
Item [75], Inventors, -- Brian J. Martinell -- should be added.

Signed and Sealed this

Tenth Day of January, 2006

JON W. DUDAS
*Director of the United States Patent and Trademark Office*